(12) United States Patent
Shen et al.

(10) Patent No.: US 12,306,356 B2
(45) Date of Patent: May 20, 2025

(54) X-RAY SYSTEMS INCLUDING AN ADAPTER

(71) Applicant: Varex Imaging Corporation, Salt Lake City, UT (US)

(72) Inventors: Xiaoyang Shen, Salt Lake City, UT (US); Marcelo C Costa, Draper, UT (US); Cody W Bussey, West Jordan, UT (US); Oliver Patrick Morris, San Francisco, CA (US); Matt McCabe, Kearns, UT (US); Carlo Tognina, Salt Lake City, UT (US); Andrew Hartmann, Midvale, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 198 days.

(21) Appl. No.: 17/711,743

(22) Filed: Apr. 1, 2022

(65) Prior Publication Data

US 2023/0009801 A1  Jan. 12, 2023

Related U.S. Application Data

(60) Provisional application No. 63/220,941, filed on Jul. 12, 2021.

(51) Int. Cl.
*G01T 1/175* (2006.01)
*G01T 1/24* (2006.01)

(52) U.S. Cl.
CPC .............. *G01T 1/175* (2013.01); *G01T 1/243* (2013.01); *G01T 1/244* (2013.01)

(58) Field of Classification Search
CPC .......... G01T 1/175; G01T 1/243; G01T 1/244
See application file for complete search history.

(56) References Cited

U.S. PATENT DOCUMENTS

2003/0124903 A1  7/2003  Inagaki et al.
2006/0104416 A1  5/2006  Kump et al.
(Continued)

FOREIGN PATENT DOCUMENTS

CN  102846327 A  1/2013
CN  103682903 B  3/2014
(Continued)

OTHER PUBLICATIONS

EP Appl. No. 4119058, Search Report dated Nov. 30, 2022 (forms 1503, 1507, 1703—7 pages).
(Continued)

*Primary Examiner* — Dani Fox
*Assistant Examiner* — Fani Polyzos Boosalis
(74) *Attorney, Agent, or Firm* — Dorsey & Whitney LLP

(57) ABSTRACT

Some embodiments include an x-ray system, comprising: an x-ray detector comprising: a housing; a sensor array configured to generate an image in response to incident x-ray radiation and disposed in the housing; a control circuit coupled to the sensor array, configured to control the sensor array, and disposed in the housing; and a first connector interface disposed on an exterior of the housing and electrically connected to the control circuit; an adapter comprising: a second connector interface configured to physically and electrically mate with the first connector interface; a third connector interface having at least one of a physical configuration and an electrical configuration different from the first connector interface; and a plurality of electrical connections between the second connector interface and the third connector interface.

20 Claims, 9 Drawing Sheets

(56) References Cited

U.S. PATENT DOCUMENTS

| | | | |
|---|---|---|---|
| 2010/0284521 A1* | 11/2010 | McBroom | A61B 6/4233 378/204 |
| 2011/0254563 A1 | 10/2011 | Liu et al. | |
| 2012/0042112 A1 | 2/2012 | Thomas, III et al. | |
| 2012/0250825 A1 | 10/2012 | Yoshida et al. | |
| 2012/0318991 A1* | 12/2012 | Ohta | A61B 6/4488 250/336.1 |
| 2013/0003932 A1 | 1/2013 | Nishino | |
| 2016/0061970 A1* | 3/2016 | Asai | G01T 1/175 702/182 |
| 2019/0282185 A1 | 9/2019 | Gregerson | |

FOREIGN PATENT DOCUMENTS

| | | | |
|---|---|---|---|
| CN | 204947279 U | 1/2016 | |
| JP | 2008256685 A * | 10/2008 | A61B 6/4233 |

OTHER PUBLICATIONS

EP Appl. No. 4119058, Examination Report dated Aug. 6, 2024 (forms 2001, 2906—4 pages).

CN Appl. No. 115623292 (Published as CN202210796893), Search Report dated Aug. 16, 2024 (3 pages).

CN Appl. No. 115623292 (Published as CN202210796893), First Office Action dated Aug. 16, 2024 (8 pages).

CN Appl. No. 115623292 (Published as CN 202210796893), Response to First Office Action dated Dec. 16, 2024 (11 pages).

"DRTECH EVS 2430W / EVS 2430GW Safety and Regulatory Information with User's Manual," Feb. 22, 2017, XP055983342, Retrieved from the Internet: URL:https://fccid.io/RNH-EVS2430W/User-Manual/UserManual-3367047.pdf (102 pages).

Gong Weijia, Southeast University Press. Understanding Lines and Communication. pp. 169-173. Year: 2020.

* cited by examiner

X-RAY SYSTEMS INCLUDING AN ADAPTER

X-ray detectors may be used to generate two-dimensional images or video in response to incident x-rays. The x-ray detectors may be designed according to a specific specification, such as a customer's specification. Different designs, such as different customers, may have different specifications. As a result, the same x-ray detector may need to be redesigned to operate in different systems, such as systems of different customers.

DETAILED DESCRIPTION

Some embodiments relate to x-ray systems including an adapter. Certain x-ray imaging systems may include a hardware interface between the x-ray detector and an original equipment manufacturer (OEM) imaging system. This interface can provide the connections necessary for power, image data to an external device, battery charging, detector diagnostics, grounding, synchronization, detector location, power management, and more. The connectors necessary for the interface can be custom for each OEM system. However, to provide a reliable interface, connectors need to be compatible on the x-ray detector and the OEM system. Therefore, a single connector might not work in different OEM systems.

This external connector may take the form of spring-loaded metallic pins, or metal pads that interface with an external spring-loaded pin, or any other type of connection that may be used by the OEM system. These quick disconnect connector types may be exposed to a lot of wear and tear, such as inadvertent bodily fluids, cleaning agents, or submersion in water. As a result, there is a risk of corrosion of the connector components due to environmental factors.

In addition, a user may have an installed base of products, which may be expensive to develop. Providing a new x-ray detector with improved capabilities may result in other components of the user's system needing to be replaced to be compatible with the new x-ray detector, which could increase the costs of upgrading the system.

An x-ray detector with an adapter as described herein may alleviate these and other issues.

Figure 1:
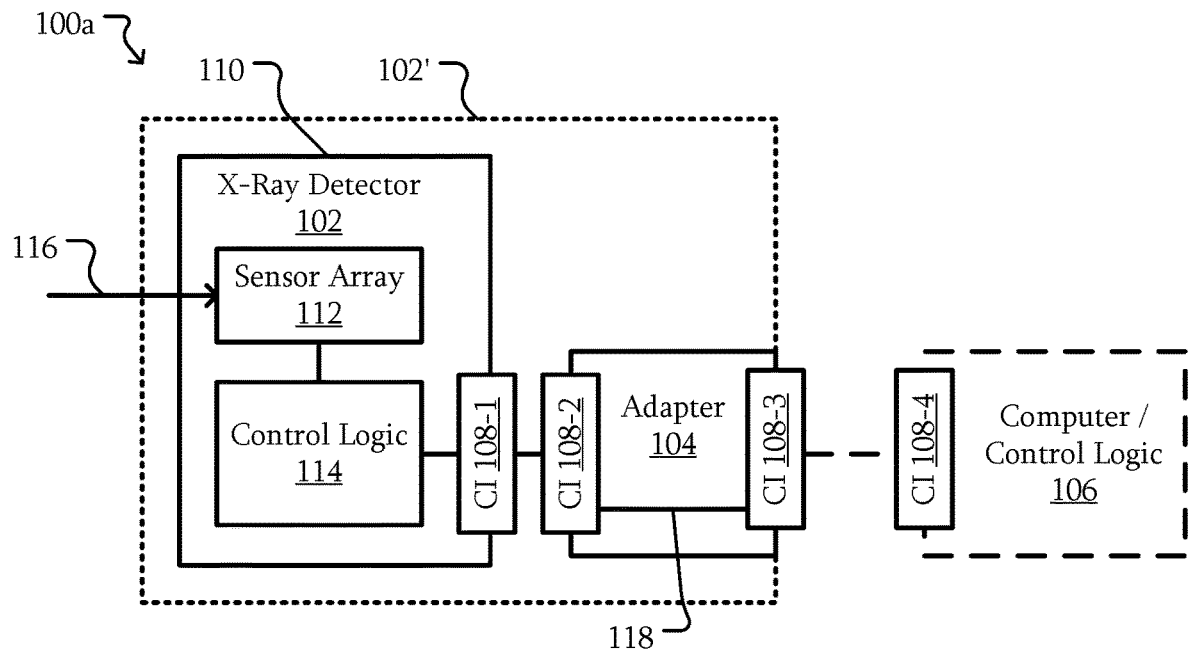
FIG. 1 is a block diagram of an x-ray system including an adapter according to some embodiments.

FIG. 1 is a block diagram of an x-ray system including an adapter according to some embodiments. In some embodiments, an x-ray system 100a includes a modular x-ray detector 102'. The modular x-ray detector 102' includes an x-ray detector (XRD) 102 and an adapter 104. The x-ray detector 102 and the adapter 104 are integrated together to form the modular x-ray detector 102'.

The x-ray detector 102 is a device configured to acquire data in response to incident x-rays. In some embodiments, the data may include image data, video data, or the like.

The x-ray detector 102 includes a housing 110, a sensor array 112, a control logic 114, and a first connector interface 108-1. The housing 110 is configured to encapsulate the sensor array 112 and the control logic 114.

The sensor array 112 is configured to generate an image in response to incident x-ray radiation and disposed in the housing. The sensor array 112 may include a variety of sensors configured to generate data based on incident x-rays. The sensor array 112 may include direct conversion sensors, indirect conversion sensors and x-ray conversion materials (e.g., scintillator materials), or the like.

The control logic 114 is disposed in the housing and coupled to the sensor array 112. The control logic 114 is configured to control the sensor array 112. The control logic 114 may include a general purpose processor, a digital signal processor (DSP), an application specific integrated circuit (ASIC), a microcontroller, a programmable circuit device (e.g., field-programmable gate array (FPGA)), discrete circuits, a combination of such devices, or the like. In addition, other interface devices, such as circuit chipsets, hubs, memory controllers, communication interfaces, or the like may be part of the control logic 114 to connect the control logic 114 to internal and external components of the x-ray detector 102.

The first connector interface 108-1 is disposed at least partially on an exterior of the housing 110. The first connector interface 108-1 is electrically connected to the control logic 114.

The adapter 104 is a device with at least two connector interfaces. Here, the adapter 104 includes a second connector interface 108-2 and a third connector interface 108-3. The second connector interface 108-2 is configured to physically and electrically mate with the first connector interface 108-1. In some embodiments, the first connector interface 108-1 and the second connector interface 108-2 have the same number of electrical contacts. The first connector interface 108-1 and the second connector interface 108-2 may be configured according to the same connector interface specification. For example, the first connector interface 108-1 and the second connector interface 108-2 may be configured according to a physical specification of a standardized connector interface such as Universal Serial Bus (USB), Ethernet, fiber optic connectors, or the like. However, in other embodiments, the first connector interface 108-1 and the second connector interface 108-2 may be proprietary connector interfaces.

The third connector interface 108-3 has at least one of a physical configuration and an electrical configuration different from the first connector interface 108-1. The physical configuration includes the location of contacts, the shape of the housing, or the like. The electrical configuration includes configurations of the contacts as a power supply, ground, transmission line, high or low impedance input or output, or the like. While the third connector interface 108-3 may be any of the variety of connection interfaces similar to the first connector interface 108-1 and second connector interface 108-2, the third connector interface 108-3 in any particular embodiment is different from the first connector interface 108-1 and second connector interface 108-2.

The adapter 104 includes electrical connections 118 between the second connector interface 108-2 and the third connector interface 108-3. As will be described in further detail below, the electrical connections 118 may include wires, circuits, terminations, signal conditioning, power converters, control logic, printed circuit boards (PCBs), processors, or the like.

The modular x-ray source 102' may be coupled to a computer/control logic 106. The computer/control logic 106 may include a system in which the modular x-ray source 102' may be installed. For example, the computer/control logic 106 may include a bucky of an x-ray system, a mobile cart, a charging station, power supply, or the like. The computer/control logic 106 includes fourth connection interface 108-4 configured to mate with the connection interface 108-3 of the modular x-ray source 102'.

FIG. 2A-2E are diagrams of electrical connections of adapters in an x-ray system according to some embodiments. In FIGS. 2A-2E, the physical interfaces of the connection interfaces 108-1 and 108-2 are referred to as the physical interface PHY1/2 and the conductors 122 represent the electrical connections formed when the contacts of the connection interfaces 108-1 and 108-2 are mated. Similarly, the physical interfaces of the connection interfaces 108-3 and 108-4 are referred to as the physical interface PHY3/4 and the conductors 124 represent the electrical connections formed when the contacts of the connection interfaces 108-3 and 108-4 are mated. The number of conductors 122 and/or 124 are used as examples.

In some embodiments, some contacts of the connector interface 108-3 are directly connected to corresponding contacts 108-2 as illustrated by the direct connection between conductors 122 and 124. Any number of these direct connections may be included in the adapter 104 including zero, less than all, and all.

Figure 2A:
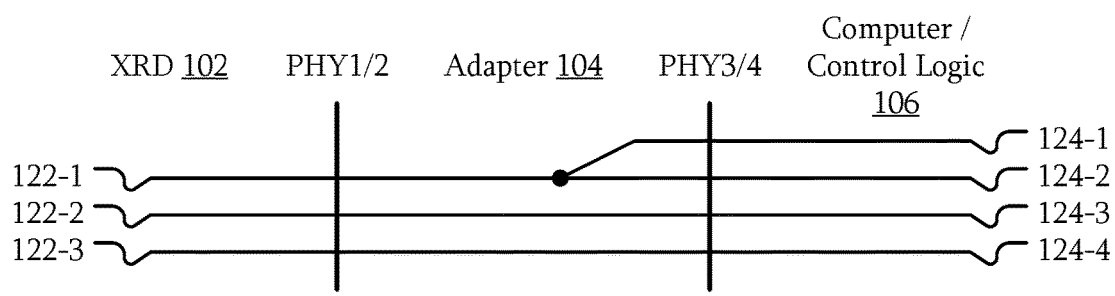
FIG. 2A-2E are diagrams of electrical connections of adapters in an x-ray system according to some embodiments.

Referring to FIGS. 1 and 2A, in some embodiments, the connector interfaces 108-1 and 108-2 have fewer contacts than the connector interface 108-3 and 108-4. Thus, fewer conductors 122 are formed than conductors 124. In some embodiments, within the adapter 104, electrical connections electrically connect multiple contacts of the third connector interface 108-3 to a single contact of the second connector interface 108-2. Here, conductors 124-1 and 124-2 are electrically connected together in the adapter 104 to conductor 122-1. While, connecting two contacts of the third connector interface 108-3 to one contact of the second connector interface 108-2 is used as an example, in other embodiments, the numbers may be different.

In a particular example, the conductors 122-1, 124-1 and 124-2 may be used for ground or another voltage. The adapter 104 and the conductor 122-1 may be configured to handle the combined current passing through conductors 124-1 and 124-2.

Figure 2B:
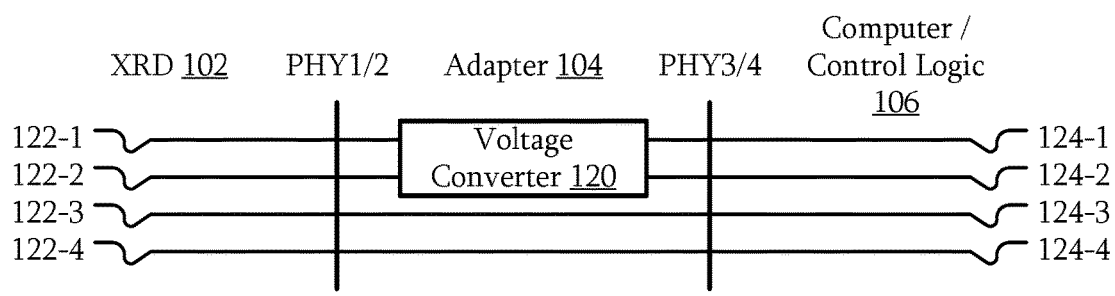

Referring to FIGS. 1 and 2B, in some embodiments, the adapter 104 includes a voltage converter 120. For example, the computer/control logic 106 may be configured to provide a power supply voltage, such as 24 volts (V) across conductors 124-1 and 124-2. The voltage converter 120 within the adapter 104 may be configured to convert the voltage into a different voltage across conductors 122-1 and 122-2. For example, the voltage converter 120 may include a direct current (DC) to DC converter configured to convert the 24 V to 19 V. In another example, the voltage converter may include an alternating current (AC) to DC converter configured to convert 48 VAC to 19 VDC. While 19 V has been used as an example, in other embodiments the voltage may be different. In addition, a single voltage may be converted into multiple voltages within the adapter 104. In some embodiments, the voltage converter 120 may be configured to regulate the voltage, prevent over voltages, or the like.

Figure 2C:
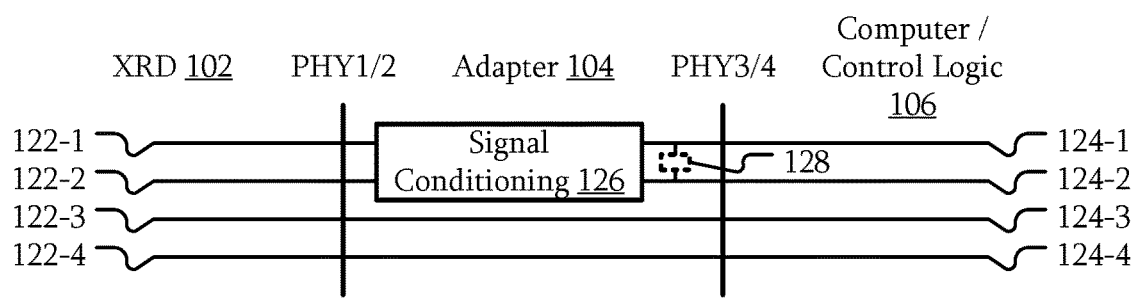

Referring to FIGS. 1 and 2C, in some embodiments, the computer/control logic 106 may be expecting a particular load at the interface PHY3/4. For example, conductors 124-1 and 124-2 may form a twisted pair, a transmission line, an impedance controlled structure, or the like. The conductors 124-1 and 124-2 may be coupled to a signal conditioning circuit 126. The signal conditioning circuit 126 may be configured convert signals from one format to a different format. For example, the signal conditioning circuit 126 may be configured to transform a signal from a balanced connection to a single-ended connection or vice versa. In other embodiments, a load 128 may terminate a transmission line formed by conductors 124-1 and 124-2. In other embodiments, the signal conditioning circuit 126 may be configured to buffer, amplify, or otherwise regenerate a signal on conductors 124. The signal conditioning circuit 126 may be unidirectional or bidirectional.

Figure 2D:
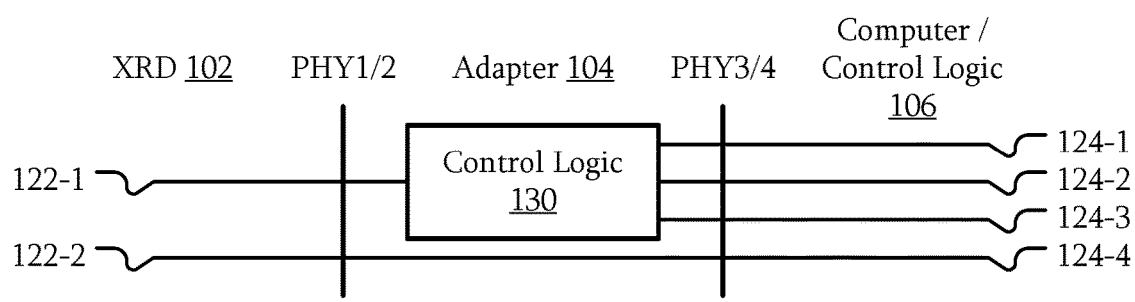

Referring to FIGS. 1 and 2D, in some embodiments, the adapter 104 may include control logic 130. The control logic 130 may include a general purpose processor, a DSP, an ASIC, a microcontroller, a programmable logic device such as an FPGA, discrete circuits, a combination of such devices, or the like. In addition, other interface devices, such as logic chipsets, hubs, memory controllers, communication interfaces, or the like may be part of the control logic 130 to connect the control logic 130 to internal and external components of the adapter 104.

In this example, the control logic 130 may be coupled to the conductors 122-1 and 124-1 to 124-3. The control logic 130 may be configured to present a first functional interface at the third connector interface 108-3. For example, the conductors 124-1 to 124-3 may include a communication interface such as a serial or parallel interface, independent signal interfaces for signals such as reset signals, trigger signals, a network interface, or the like. The control logic 130 may be configured to present a second functional interface at the second connector interface 108-2. The control logic 130 may be configured to transform the content of the signals into a different format on conductor 122-1 for the x-ray detector 102, convert between different protocols, convert the timing of the signals, or the like. The control logic 130 may be configured to convert signals from the x-ray detector 102 on conductor 122-1 into the format expected by the computer/control logic 106. In a particular example, the conductors 124 may include an Ethernet interface. The control logic 130 may be configured to implement a communication stack to extract information transmitted from the computer/control logic 106 and/or encapsulate information from the x-ray detector 102 to be transmitted to the computer/control logic 106.

Figure 2E:
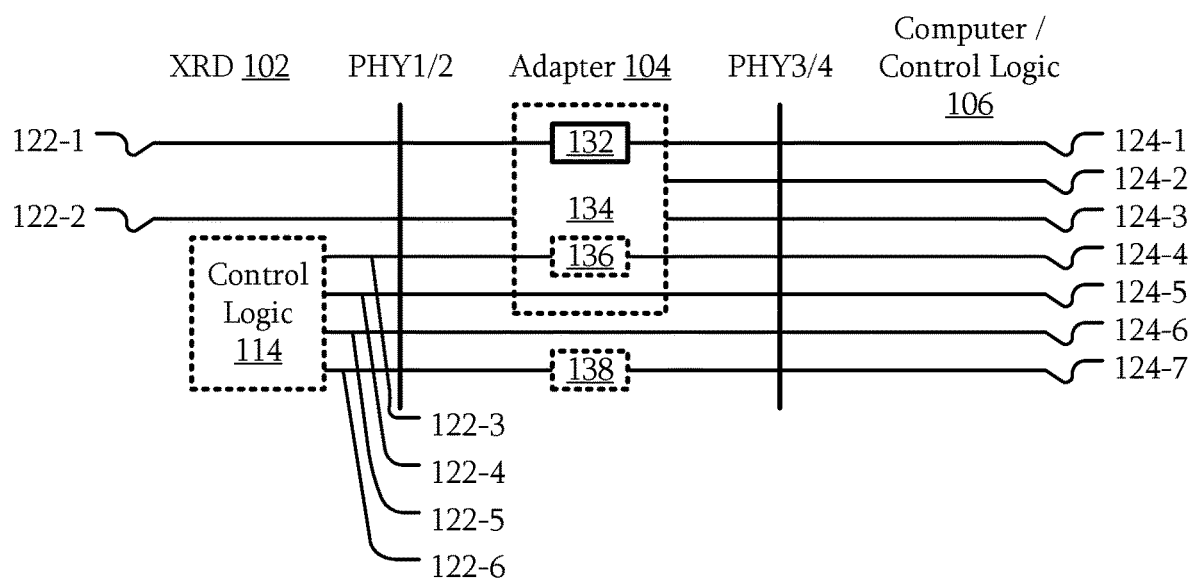

Referring to FIGS. 1 and 2E, in some embodiments, an adapter 104 may include any combination of the above examples. Here, the adapter 104 includes a variety of different configurations of the circuits described above. For example, circuit 132 may include signal conditioning (similar to the signal conditioning circuit 126 in FIG. 2C). The circuit 136 may include voltage conversion (similar to the voltage converter 120 in FIG. 2B). The circuit 134 may include control logic (similar to the control logic 130 in FIG. 2D). The circuits 132 and 136 may be part of the control logic of circuit 134. A circuit 138 may have functions similar to the control logic 130 of FIG. 2D, the voltage converter 120 in FIG. 2B, the signal conditioning circuit 126 in FIG. 2C, or the like; however, the circuit 138 may be separate from the circuit 134.

In some embodiments, at least some processing or conversion of the signals from the computer/control logic 106 may be performed in the control logic 114. For example, the adapter 104 may be configured to perform some conversion, such as the termination or signal conditioning described above while the control logic 114 is configured to convert the functional formats the signals received from the computer/control logic 106 through the adapter 104. That is, the adapter 104 may convert the physical configuration and electrical interfaces while the control logic 114 converts the content of the signals.

In some embodiments, the signals that are converted may be particular to the acquisition of data using x-rays. For example, one of the signals may be a trigger signal indicating that the x-ray detector 102 should acquire a data based on incident x-rays 116. In another example, the signal may include a signal from the x-ray detector 102 indicating that a pulse of x-rays 116 should be generated using the computer/control logic 106. Regardless, the adapter 104 may be configured to convert between the formats expected by the x-ray detector 102 and the computer/control logic 106.

In another example, the signals may include synchronization signals to synchronize the x-ray detector 102 with other components of the system 100a. In another example, the signals may include signals to wake up the x-ray detector 102 and get an X-ray rotor of an x-ray source spinning before an acquisition.

In another example, the adapter 104 may be configured to implement a hot swap function, where the adapter 104 may be replaced without stopping, shutting down or powering down, or rebooting the x-ray system or x-ray detector 102. The modular x-ray detector 102' may be configured to be hot swappable. For example, the adapter 104 may include a configuration of contacts to enable hot swapping, such as contacts for power for the adapter 104 that connect before other contacts of the adapter 104, control logic 130 that may inform the control logic 114 of the x-ray detector 102 of the configuration of the adapter 104, or the like. The control logic 130 may be configured to control the application of power to the x-ray detector 102, initiate a startup sequence, or the like.

Although in some embodiments, the number of contacts for the third connector interface 108-3 has been described as being larger than the number of the contacts of the first and second connector interface 108-1 and 108-2, in other embodiments the number may be smaller.

In some embodiments, one or more conductors 124 may indicate a status of the modular x-ray detector 102'. For example, the status of a conductor 124, a voltage applied to it, or the like may indicate whether the modular x-ray detector 102' is installed in a mobile cart, a bucky table, a bucky wall, or the like. In some embodiments, the adapter 104 may be configured to transform information from the x-ray detector 102 such as battery information, charging state, and/or receive commands related to the battery or other power systems of the x-ray detector 102. In another example, a signal on the conductor 124 may be forwarded to the control logic 114, processed into a command for the control logic 114, or the like to implement functions such as putting the x-ray detector 102 in a sleep state when placed in a mobile cart, waking up the x-ray detector 102 when being removed from the mobile cart, or the like.

The variety of functions, electrical interfaces, or the like may be different for a variety of applications of the modular x-ray detector 102'. The modular adapter 104 allows for the same or substantially the same x-ray detector 102 to be used with multiple different systems, each having unique requirements for power, pinout, electrical configuration, communication formats and protocols, or the like. The adapter 104 may be changed rather than the internal hardware of the x-ray detector 102 to accommodate a different system. Mechanical and/or electrical changes to the x-ray detector 102 may affect certifications such as electromagnetic compatibility (EMC), Underwriter Laboratories (UL) certifications, ingress protection certifications, or the like. The use of the adapter 104 may avoid such mechanical and/or electrical changes.

In some embodiments, only hardware related differences are handled in the adapter 104. For example, voltage conversion, pinout, terminations, or the like may be converted in the adapter 104 while conversions of the communication protocols, functional interfaces, or the like may be implemented in the control logic 114. However, the implementation in the control logic 114 may be much less expensive to change to accommodate a new third connector interface 108-3 for a different system than redesigning the hardware of the x-ray detector 102. In some embodiments, some mechanical aspects of the x-ray detector 102 may be changed; however, the electronics of the x-ray detector 102 may remain the same. For example, the housing 110 of the x-ray detector 102 may be changed while maintaining the design of the internal electronics.

In some embodiments, the combination of the adapter 104 and the control logic 114 allows for the various contacts of the third connector interface 108-3 to be configurable. For some systems, the contacts may operate in a first manner while a change to software or firmware in the control logic 114 and/or a control logic 130, 134, or 138 of the adapter 104 allows for the function of the contacts to be changed without a hardware change to the x-ray detector 102.

Figure 3A:
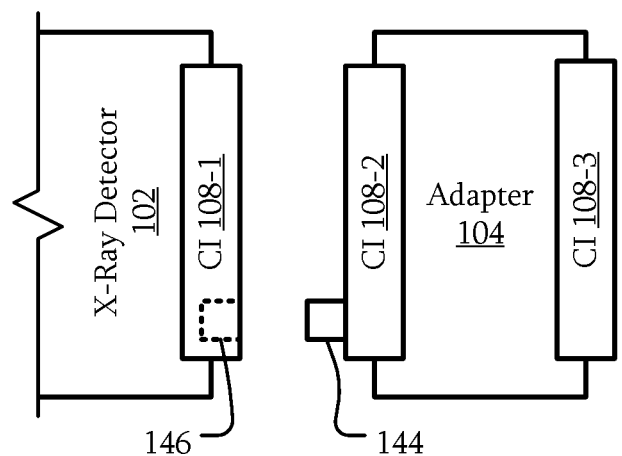
FIG. 3A is a block diagram of a first connector interface and a second connector interface of an x-ray system with alignment structures according to some embodiments.

FIG. 3A is a block diagram of a first connector interface and a second connector interface of an x-ray system with alignment structures according to some embodiments. In some embodiments, the first connector interface and 108-1 the second connector interface 108-2 include at least one alignment structure pair 144 and 146. An alignment structure pair 144 and 146 may include complementary structures configured to place the contacts of the connector interfaces 108-1 and 108-2 in alignment to be mated. For example, the alignment structure pair 144 and 146 may include a post and a corresponding opening, recess, complementary structures, or the like. Other examples of alignment structures include a physical locating feature such as a pin or a cone, or a magnetic locating feature, or any other system such that the connector interface 108-1 and connector interface 108-2 are aligned properly. Although one alignment structure pair 144 and 146 is used as an example, in other embodiments, multiple alignment structure pairs 144 and 146, including different types, may be included.

Figure 3B:
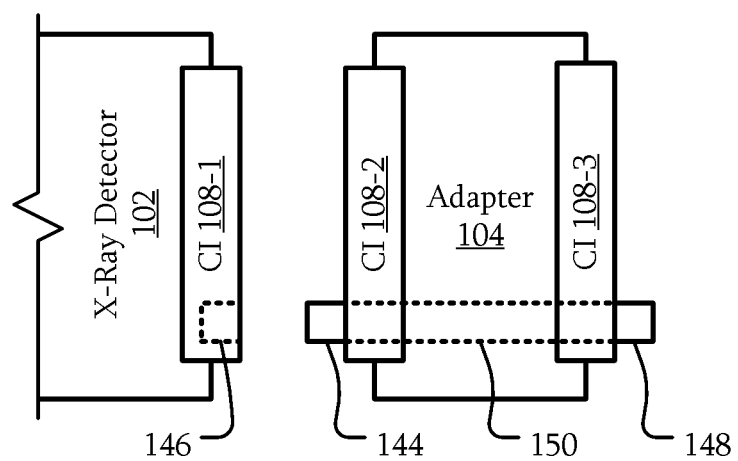
FIG. 3B is a block diagram of a third connector interface of an x-ray system with alignment structures according to some embodiments.

FIG. 3B is a block diagram of a third connector interface of an x-ray system with alignment structures according to some embodiments. In some embodiments, the third connector interface 108-3 includes an alignment structure 148. Similar to the alignment structure pair 144 and 146, the alignment structure 148 may be configured to mate with a corresponding structure of a connector interface 108-4.

Similar to the alignment structure pair 144 and 146, the alignment structure 148 may have similar features, such as physical locating features.

In some embodiments, the alignment structures 144 and 148 are part of a single alignment structure 150 that extends through the adapter 104 from the second connector interface 108-2 to the third connector interface 108-3. In some embodiments, the alignment structure 150 may reduce an effect on mechanical tolerances due to the use of the adapter 104. For example, a specification for the connector interface 108-3 may establish a particular mechanical tolerance for the position of the connector interface 108-3 relative to the housing 110 of the x-ray detector 102. The use of the adapter 104 may otherwise increase the mechanical tolerance as additional movement relative to the housing 110 may be introduced by the additional mechanical structures between the housing 110 and the connector interface 108-3. The alignment structure 150 may allow for the alignment structure 148 to have a reduced mechanical tolerance relative to the housing 110 as the alignment structure 150 may be attached directly to the housing 110 or other structure such that any increase in tolerance due to the use of the adapter 104 may be reduced. While the alignment structures 144 and 148 or their features may be mechanically coupled or made from the same material as alignment structure 150, the features of the alignment structures 144 and 148 may be different.

In some embodiments, the various alignment structures described herein may include structural features on an overmold, parts attached directly to an internal printed circuit board (PCB), structures co-molded with the PCB inside the overmold, or additional parts not molded in that are attached to the connector interfaces 108 via adhesives, screws, or other fasteners, or the like. These or other features may also be used to mount the connector rigidly to the x-ray detector 102 via screw holes or other mounting features or fasteners. The various alignment structures 144, 146, and 148 may include a post, an opening, a recess, a keyed feature, or locking feature with complementary structures for a mating connector.

In some embodiments, the alignment structure 150 may include magnetic components that help align the third connector interface 108-3 to the fourth connector interface 108-4.

In some embodiments, the various alignment structures 144, 146, 148, and 150 may be electrically connected to the adapter 104 and/or the x-ray detector 102. For example, one or more of the alignment structures 144, 146, 148, and 150 may be electrically connected to ground.

Figure 3C:
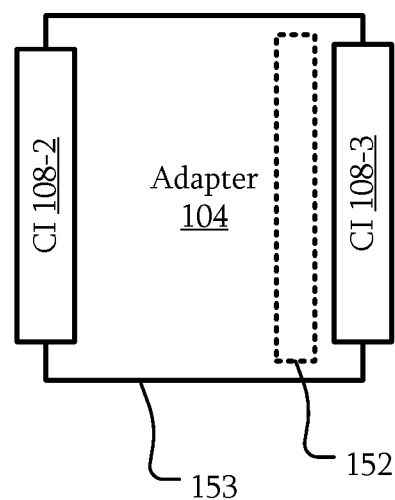
FIG. 3C is a block diagram of a stiffener of an adapter of an x-ray system according to some embodiments.

FIG. 3C is a block diagram of a stiffener of an adapter of an x-ray system according to some embodiments. In some embodiments, the adapter 104 may include a stiffener 152. The stiffener 152 may include a plate, rod, bar, or the like formed of a material such as metal, plastic, or the like having a stiffness greater than the body 153 of the adapter 104. As a result, planar tolerances and signal integrity for signals on the connector interface 108-3 may be improved.

Figure 4A:
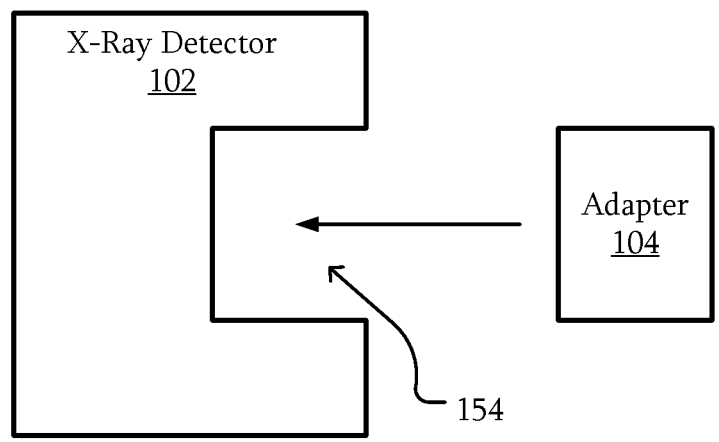
FIGS. 4A and 4B are block diagrams of an x-ray system with an adapter and an x-ray detector recess according to some embodiments.
Figure 4B:
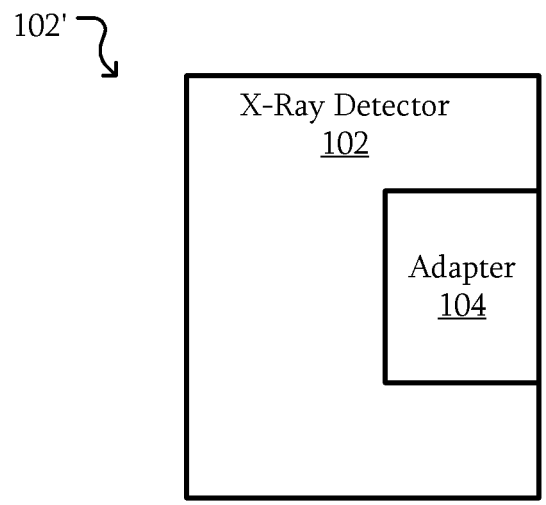

FIGS. 4A and 4B are block diagrams of an x-ray system with an adapter and an x-ray detector recess according to some embodiments. In some embodiments, the housing 110 of the x-ray detector 102 includes a recess 154. The adapter 104 is configured to be integrated with the x-ray detector 102 in the recess 154. The first connector interface 108-1 may be disposed in the recess 154. The third connector interface 108-3 may be disposed such that the modular x-ray detector 102' has a form factor substantially the same as a conventional x-ray detector.

In some embodiments, the recess 154 is configured to receive different types of adapters 104. For example, a first type of adapter 104 integrated with the x-ray detector 102 may result in the modular x-ray detector 102' having a form factor and functions of a first conventional x-ray detector. A second type of adapter 104 may be integrated with the same x-ray detector 102 and the resulting modular x-ray detector 102' may have the form factor and functions of a second conventional x-ray detector or a new type of x-ray detector. That is, the same x-ray detector 102 may be used while the different adapter 104 transforms the modular x-ray detector 102' into a different form factor.

Figure 5A:
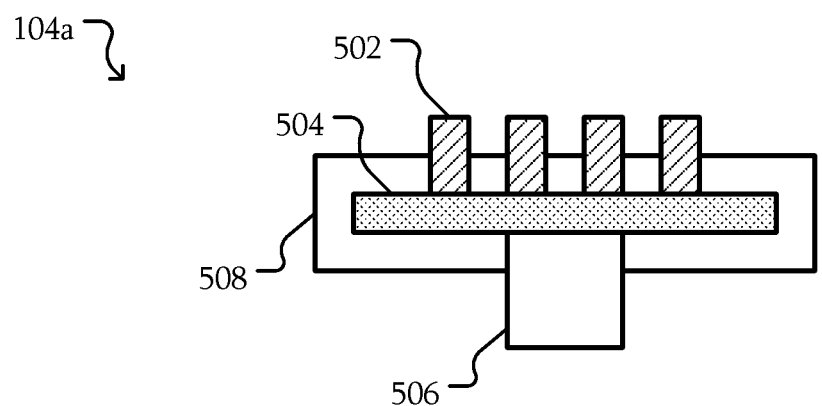
FIGS. 5A-5D are cross-sectional views of adapters according to some embodiments.

FIGS. 5A-5D are cross-sectional views of adapters according to some embodiments. Referring to FIG. 5A, in some embodiments, an adapter 104a may be similar to the adapter 104 described above. The adapter 104a includes a PCB 504. Conductors 502 are electrically connected to the PCB 504, resulting the at least part of the third connector interface 108-3. A connector 506 may be electrically connected to the PCB 504. The connector 506 may form at least part of the second connector interface 108-2. Although contacts 502 and a connector 506 have been used as examples of parts of a connector interface 108, in other embodiments, contacts, connectors, other electrical connections, or the like may be electrically connected to the PCB 504 to form at least part of the respective connector interface 108-2 or 108-3. In some embodiments, an overmold 508 may be formed around the PCB 504. The PCB 504 may include other components and electrical connections to create the various connections, circuits, or the like as described above. In some embodiments, the PCB 504 may also act as the stiffener 152 (in FIG. 3C) while in other embodiments, a separate stiffener 152 may be included. The overmold 508 may include a polymer substrate, such plastic, isoprene, or rubber which can provide environment protection or contribute to a specific ingress protection rating for the adapter, x-ray detector, or x-ray system.

Figure 5B:
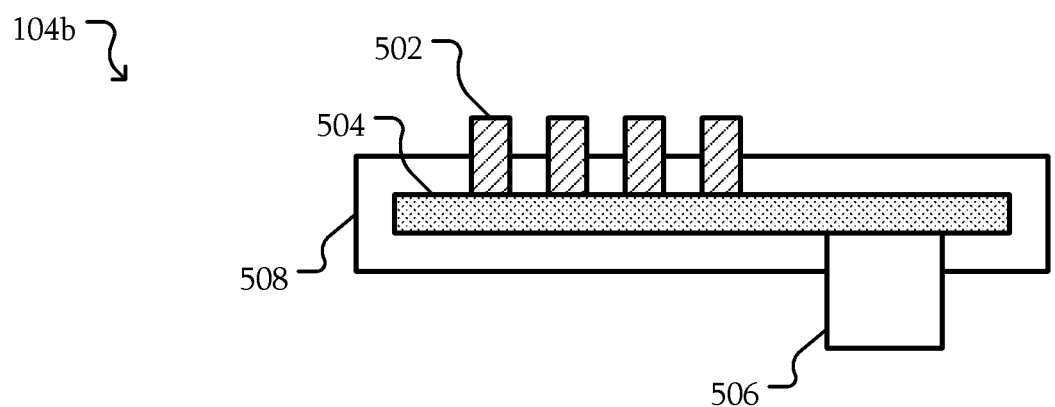

Referring to FIG. 5B, in some embodiments the adapter 104b may be similar to the adapter 104a. However, the connector 506 may be offset from the contacts 502.

Figure 5C:
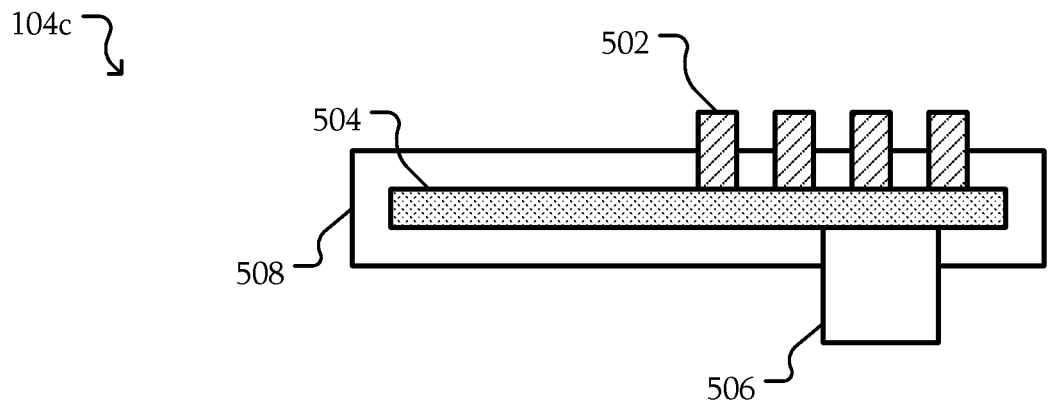

Referring to FIG. 5C, in some embodiments, the adapter 104c may be similar to the adapter 104b. However, the contacts 502 or a similarly situated connector may be disposed in a different location on a similar adapter 104b. The position of the connector 506 and the overmold 508 may be the same. As a result, the adapter 104b may be integrated with the same x-ray detector 102 regardless of the position of the contacts 502. However, the different contacts 502 and/or different circuitry within the same form factor of the adapter 104b may allow for the modular x-ray detector 102' to have the same form and function of multiple different x-ray detectors.

Figure 5D:
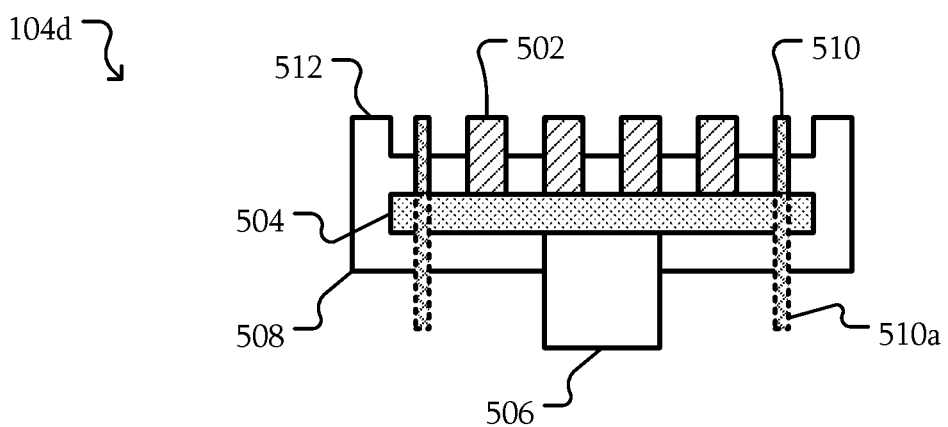

Referring to FIG. 5D, in some embodiments, the adapter 104d may be similar to the adapters 104a-104c. However, the adapter 104d includes alignment structures 510 and 512. The alignment structure 510 may be attached to the PCB 504. The alignment structures 512 may be part of the overmold 508. In some embodiments, the alignment structure 510 may extend through the PCB 504 and the overmold 508. A portion 510a of the alignment structure 510 may form an alignment structure for the connector interface 108-2. In some embodiments, the alignment structures 510 and 512 may be similar to the alignment structures 144, 146, 148, and 150 (in FIGS. 3A and 3B).

In some embodiments, the adapter 104 or the like may improve a usable lifetime of the modular x-ray detector 102'.

For example, as the adapter 104 is a modular component, it may be replaced after portions are worn, broken, corroded, or otherwise damaged.

Although a single adapter 104 has been used as an example, in other embodiments, multiple adapters may be cascaded or stacked, disposed side by side, or the like to create a desired connector interface on a modular x-ray detector 102'.

Although a single PCB 504 has been used as an example of a PCB in an adapter 104, in other embodiments, multiple PCBs 504 may be part of an adapter 104. For example, one PCB 504 may be electrically connected to the contacts 502 while a different PCB 504 is attached to the connector 506. Other wires, cables, connectors, or the like may electrically connect the two PCBs 504 within adapter 104.

In some embodiments, the adapter 104 may be used for other replaceable components such battery connectors, external buttons or displays, user interface panels, or the like of the modular x-ray detector 102'. As a result, a variety of different replaceable components may be used by selecting the appropriate adapter 104.

Although the adapters 104 have been illustrated as having contacts 502 in the same plane as the connector 506, in other embodiments, the contacts 502 and the connector 506 may be disposed in different orientations. For example, the contacts 502 and the connector 506 may be disposed at right angles to each other, rotated by a different angle, or the like.

Figure 6A:
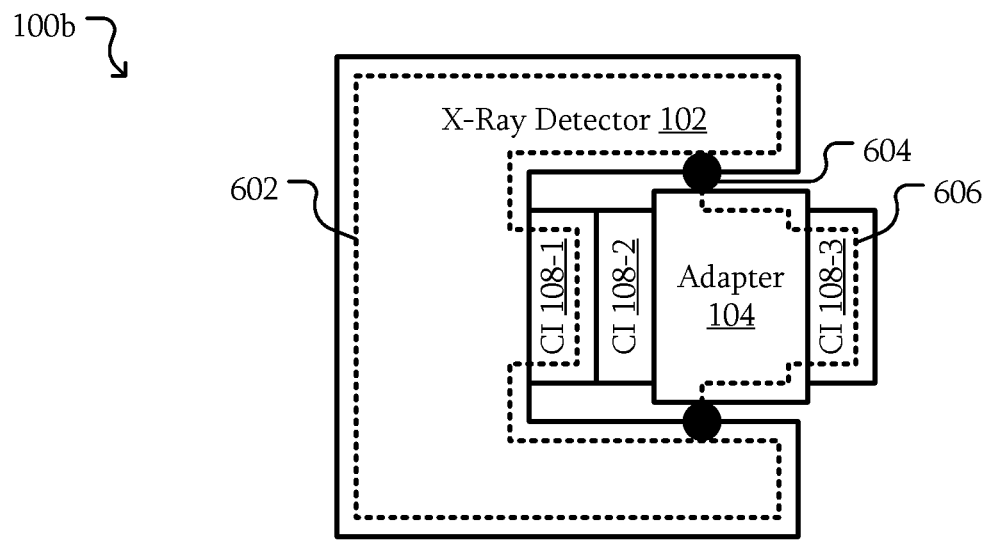
FIG. 6A-6C are block diagrams of x-ray systems with ingress protection seals according to some embodiments.
Figure 6B:
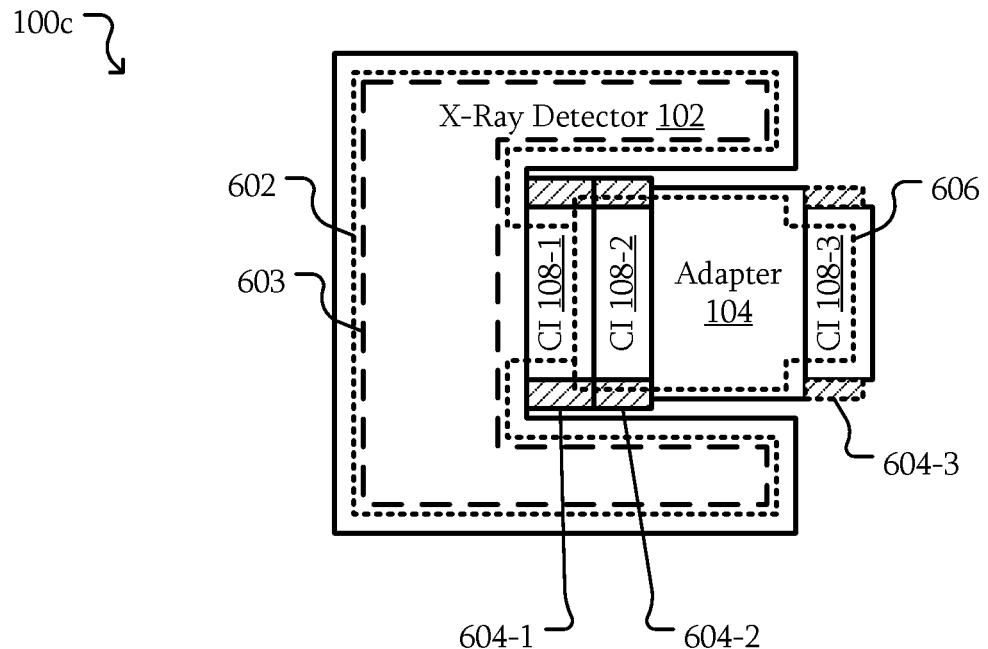
Figure 6C:
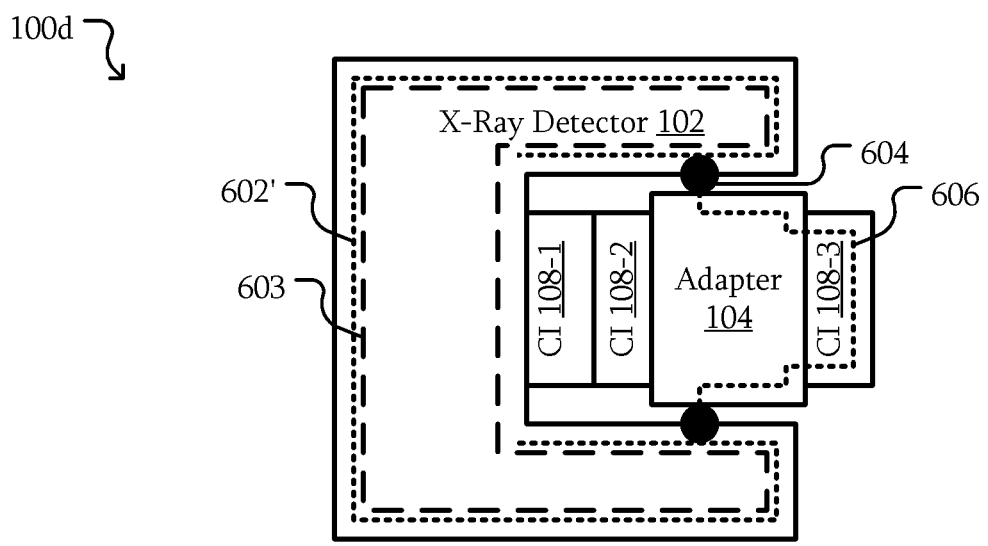

FIG. 6A-6C are block diagrams of x-ray systems with ingress protection seals according to some embodiments. Referring to FIG. 6A, in some embodiments, the x-ray system 100b may be similar to the x-ray system 100a described above. The adapter 104 may be used as part of ingress protection for the modular x-ray detector 102'.

In some embodiments, the x-ray detector 102 includes a seal 602 extending around a perimeter of the x-ray detector 102. The seal may be capable of meeting an ingress protection standard against fluid ingress, dust or other particulate ingress, debris ingress, and ingress of similar materials into the x-ray detector 102. In some embodiments, the seal 602 can have an ingress protection rating or Ingress Protection Code level of IP68 or better. Conventional x-ray detectors may be capable of meeting an Ingress Protection Code level of IP56 where the x-ray detector may be protected somewhat from dust (e.g., dust protected with limit ingress) and water jets (e.g., 12.5 mm nozzle water spray from any direction). Ingress Protection Code level refers to the protection against solid ingress represented by the first digit (e.g., 5 in IP56) and liquid ingress represented by the second digit (e.g., 6 in IP56). However, the x-ray detector with an IP56 cannot be submerged in a liquid, such as water. An x-ray detector 102 as described herein may meet or exceed Ingress Protection Code level of conventional x-ray detectors with an ingress of IP57 (where 7 refers to immersion in water for 30 minutes at 1 meter), IP67 (where 6 refers to dust tight with no ingress of dust for 2 to 8 hours), or IP68 where the x-ray detector 100 is dust tight and the x-ray detector 100 may be submerged or immersed in 1 meter or more of water for at least 60 minutes).

The adapter 104 includes a seal 606 extending around the second connector interface 108-2 and configured to form a seal with the x-ray detector 102 when the adapter 104 is attached to the x-ray detector 102. For example, a gasket 604 or other seal may connect the seal 602 to the seal 606. As a result, an interface of the first connector interface 108-1 and the second connector interface 108-2 may be sealed against fluid, dust, or other ingress. In some embodiments, features of the overmold 508 or the like as described above may form at least part of the seal 606. In some embodiments, the adapter 104 with the seal 602 and 606 can have an ingress protection rating or Ingress Protection Code level greater than or equal to the x-ray detector 102.

In some embodiments, the use of an x-ray detector 102 with the seal 602 in combination with an adapter 104 with the seal 606 may allow for a modular x-ray detector 102' with the form factor and functions of a conventional x-ray detector that was not available with ingress protection to be replaced with a new modular x-ray detector 102' with ingress protection. The modular x-ray detector 102' may be a drop-in replacement.

In some embodiments, the adapter 104 may be outside of a faraday cage 603 of the x-ray detector 102. Any weakness of the customer facing connector such as water or electromagnetic interference (EMI) leakage may not influence the integrity of the x-ray detector 102 itself.

In some embodiments even if the x-ray detector 102 is sealed, another seal is formed using the adapter 104 and the seal 606. This seal protects the interface of the first and second connector interface 108-1 and 108-2.

In some embodiments the seal 606 may bridge an EMI seal around the x-ray detector 102 through the adapter.

Referring to FIG. 6B, in some embodiments, the x-ray system 100c may be similar to the x-ray system 100b. Seals may be placed in a variety of locations. For example, gaskets 604-1 and 604-2 may be placed on the housing of the x-ray detector 102 around the first connector interface 108-1 and on the housing of the adapter 104 around the second connector interface 108-2, respectively. The gaskets 604-1 and 604-2 may mate when the connector interface 108-1 and 108-2 are mated combining the seals 602 and 606. Other structures such as gasket 604-3 may be disposed around the connector interface 108-3 such that a seal may be formed when the third connector interface 108-3 is mated with a fourth connector interface 108-4. In some embodiments, the overmold of the adapter 104 may form at least part of a seal in place of or in addition to the gaskets 604-1 to 604-3.

Referring to FIG. 6C, in some embodiments, the x-ray system 100d may be similar to the x-ray system 100b. However, the x-ray detector 102 may include a seal 602' that is not complete within the x-ray detector 102 itself. Instead, the seal 606 of the adapter 104 may complete the seal for the modular x-ray detector 102'.

In some embodiments, x-ray detector 102 with the seal 602 or 602' in combination with deal 606 can have an Ingress Protection Code level greater than conventional x-ray detectors (e.g., IP6, IP57, IP67, or the like).

Figure 7:
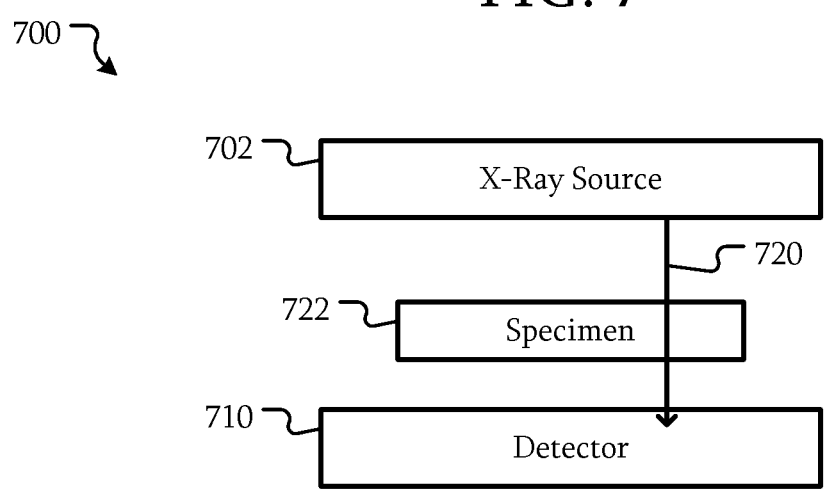
FIG. 7 is a block diagram of a 2D x-ray imaging system according to some embodiments.

FIG. 7 is a block diagram of a 2D x-ray imaging system according to some embodiments. The 2D x-ray imaging system 700 includes an x-ray source 702 and an x-ray detector 710. The detector 710 may include a modular x-ray detector 102' or the like as described above. The x-ray source 702 is disposed relative to the detector 710 such that x-rays 720 may be generated to pass through a specimen 722 and detected by the x-ray detector 710. In some embodiments, the x-ray detector 710 is part of a medical imaging system. In other embodiments, the 2D x-ray imaging system 700 may include a portable vehicle scanning system as part of a cargo scanning system.

Figure 8:
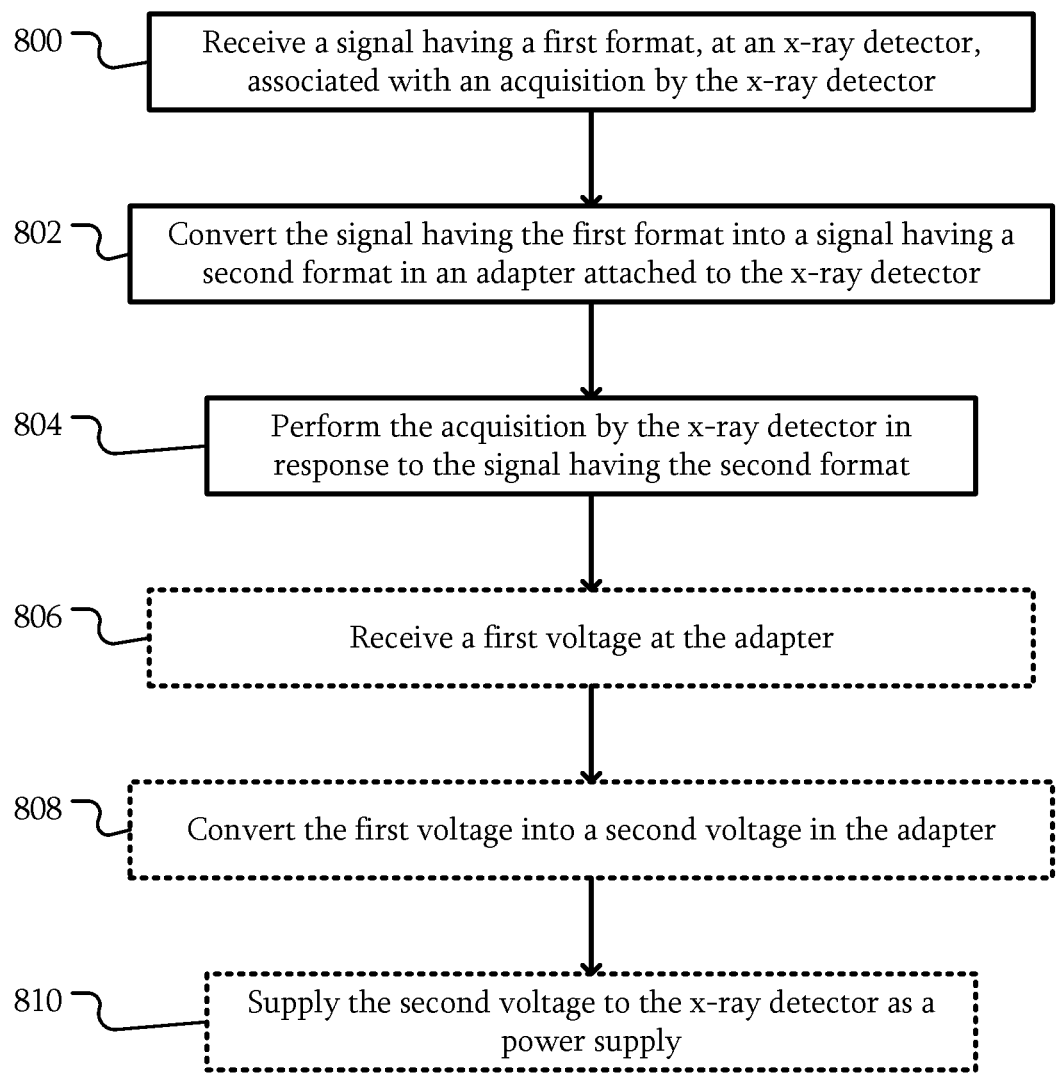
FIG. 8 is a flowchart of a technique of operating an x-ray system including an adapter according to some embodiments.

FIG. 8 is a flowchart of a technique of operating an x-ray system including an adapter according to some embodiments. Referring to FIGS. 1 and 8, in 800, a signal having a first format is received at an x-ray detector associated with an acquisition by the x-ray detector. For example, a signal from the computer/control logic 106 may be received by the adapter 104 of the modular x-ray detector 102'. The signal may be formatted to be transmitted over the physical and electrical interface of the mated connection interfaces 108-3 and 108-4.

In 820, the signal having the first format is converted into a signal having a second format in an adapter 104 attached to the x-ray detector 102. For example, the control logic 130 may transform the signal into a different protocol. In another example, the signal conditioning 120 may convert the electrical format of the signal from a balanced to a single ended format. Other conversions may be performed as described above.

In 804, the x-ray detector 102 may perform an acquisition in response to the signal having the second format. For example, as the signal may be converted to a different protocol in 802 that is understood by the x-ray detector 102, the signal may be used by the x-ray detector 802 to perform an acquisition.

In some embodiments, in 806, a voltage is received at the adapter 104. The voltage may be a voltage that is incompatible with the x-ray detector 102. In 808, the voltage may be converted in the adapter. For example, the voltage converter 120 may convert the incompatible voltage into a voltage with the range of a specification of the x-ray detector 102. In 810, that voltage may be supplied to the x-ray detector 102.

Some embodiments include an x-ray system, comprising: an x-ray detector 102 comprising: a housing 110; a sensor array 112 configured to generate an image in response to incident x-ray radiation and disposed in the housing 110; a control logic 114 coupled to the sensor array 112, configured to control the sensor array 112, and disposed in the housing 110; and a first connector interface 108-1 disposed on an exterior of the housing 110 and electrically connected to the control logic 114; an adapter 104 comprising: a second connector interface 108-2 configured to physically and electrically mate with the first connector interface 108-1; a third connector interface 108-3 having at least one of a physical configuration and an electrical configuration different from the first connector interface 108-1; and a plurality of electrical connections between the second connector interface 108-2 and the third connector interface 108-3.

In some embodiments, the first connector interface 108-1 and the second connector interface 108-2 are configured according to a standardized connector interface.

In some embodiments, the standardized connector interface is Universal Serial Bus (USB).

In some embodiments, the first connector interface 108-1 and the second connector interface 108-2 include at least one alignment structure 144, 146, 510s pair.

In some embodiments, the third connector interface 108-3 includes at least one alignment structure 148, 150, 510, 512.

In some embodiments, the at least one alignment structure 148, 150, 510, 512 includes an alignment structure 144, 148, 150, 510 extending from the second connector interface 108-2 to the third connector interface 108-3.

In some embodiments, the housing 110 of the x-ray detector 102 comprises a recess 154; and the adapter 104 is configured to be integrated with the x-ray detector 102 in the recess 154.

In some embodiments, the second connector interface 108-2 has fewer contacts than the third connector interface 108-3; and the electrical connections electrically connect a plurality of the contacts of the third connector interface 108-3 to a single contact of the second connector interface 108-2

In some embodiments, the electrical connections are configured to convert a first voltage applied to the third connector interface 108-3 to a second voltage at the second connector interface 108-2; and the first voltage is different from the second voltage.

In some embodiments, the electrical connections are configured to at least one of: convert of signals received at the third connector interface 108-3 in a first format to a second format; and convert signals received at the second connector interface 108-2 in the second format to the first format.

In some embodiments, the adapter 104 comprises control logic 130 coupled to the second connector interface 108-2 and the third connector interface 108-3; and the control logic 130 is configured to: present a first functional interface at the third connector interface 108-3; present a second functional interface at the second connector interface 108-2; and convert between the first functional interface and the second functional interface.

In some embodiments, the x-ray detector 102 comprises control logic 114 coupled to the first connector interface 108-1; and the control logic 114 is configured to: present a first functional interface at the third connector interface 108-3; present a second functional interface at the second connector interface 108-2; and convert at least one of: the first functional interface to the second functional interface; and the second functional interface to the first functional interface.

In some embodiments, the adapter 104 comprises a seal extending around the second connector interface 108-2 and configured to form a seal with the x-ray detector 102 when the adapter 104 is attached to the x-ray detector 102.

In some embodiments, the adapter 104 comprises a stiffener 152.

Some embodiments include a method, comprising: receiving a signal having a first format, at an x-ray detector 102, associated with an acquisition by the x-ray detector 102; converting the signal having the first format into a signal having a second format in an adapter 104 attached to the x-ray detector 102; and performing the acquisition by the x-ray detector 102 in response to the signal having the second format.

In some embodiments, the method further comprises receiving a first voltage at the adapter 104; converting the first voltage into a second voltage in the adapter 104; and supplying the second voltage to the x-ray detector 102 as a power supply.

In some embodiments, converting the signal having the first format into the signal having the second format in the adapter 104 comprises: presenting a first functional interface by the adapter 104; and presenting a second functional interface by the adapter 104 to the x-ray detector 102; converting information received through the first functional interface into the second format for the second functional interface.

In some embodiments, the method further comprises converting the signal having the second format into a signal having a third format in the x-ray detector 102. As described above with respect to FIGS. 2A-2E, the format of the signals received and transmitted by the x-ray detector 102' may be converted. For example, the signals may comply with a particular protocol. The adapter 104 may be configured to convert signals from that protocol to another protocol, another format, or the like. The control logic 130 is an example of a device that may perform the conversion. In another example, the signal conditioning 126 may be configured to convert the physical format of the signals.

Some embodiments include an x-ray system, comprising: means for receiving a signal having a first format, at an x-ray detector, associated with an acquisition by the x-ray detector; means for converting the signal having the first format into a signal having a second format in an adapter attached to the x-ray detector; and means for performing the acquisition by the x-ray detector in response to the signal having the second format.

Examples of the means for receiving a signal having a first format, at an x-ray detector 102, associated with an acquisition by the x-ray detector include an adapter 104.

Examples of the means for converting the signal having the first format into a signal having a second format in an adapter attached to the x-ray detector include connections of FIG. 2A, the voltage converter 120, the signal conditioning 126, the control logic 130, elements 132, 134, 136, and 138, or the like.

Examples of the means for performing the acquisition by the x-ray detector in response to the signal having the second format include the control logic 114 and the sensor array 112.

In some embodiments, the x-ray system further comprises means for presenting a first functional interface by the adapter; means for presenting a second functional interface by the adapter to the x-ray detector; and means for converting information received through the first functional interface into the second format for the second functional interface.

Examples of the means for presenting a first functional interface by the adapter include the connector interface 108-3, the control logic 130, elements 132, 134, 136, and 138, or the like.

Examples of the means for presenting a second functional interface by the adapter to the x-ray detector include the connector interface 108-2. the control logic 130, elements 132, 134, 136, and 138, or the like.

Examples of the means for converting information received through the first functional interface into the second format for the second functional interface include the control logic 130, elements 132, 134, 136, and 138, or the like.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:

1. An x-ray system, comprising:
   an x-ray detector comprising:
      a housing;
      a sensor array configured to generate an image in response to incident x-ray radiation and disposed in the housing;
      a control circuit coupled to the sensor array, configured to control the sensor array, and disposed in the housing; and
      a first connector interface disposed on an exterior of the housing and electrically connected to the control circuit; and
   an adapter comprising:
      a second connector interface configured to physically and electrically mate with the first connector interface;
      a third connector interface having at least one of a physical configuration and an electrical configuration different from the first connector interface; and
      a plurality of electrical connections between the second connector interface and the third connector interface;
   wherein at least one of:
      (a) the third connector interface includes at least one alignment structure extending from the second connector interface to the third connector interface;
      (b) the second connector interface has fewer contacts than the third connector interface, and the electrical connections electrically connect a plurality of the contacts of the third connector interface to a single contact of the second connector interface;
      (c) the electrical connections are configured to convert a first voltage applied to the third connector interface to a second voltage at the second connector interface, and the first voltage is different from the second voltage; or
      (d) the x-ray detector comprises control logic coupled to the first connector interface, and the control logic is configured to:
         present a first functional interface at the third connector interface;
         present a second functional interface at the second connector interface; and
         convert at least one of:
            the first functional interface to the second functional interface; and
            the second functional interface to the first functional interface.

2. The x-ray system of claim 1, wherein:
   the first connector interface and the second connector interface are configured according to a standardized connector interface.

3. The x-ray system of claim 2, wherein:
   the standardized connector interface is Universal Serial Bus (USB).

4. The x-ray system of claim 1, wherein:
the first connector interface and the second connector interface include at least one alignment structure pair.

5. The x-ray system of claim 1, wherein:
the third connector interface includes at least one alignment structure.

6. The x-ray system of claim 5, wherein:
the at least one alignment structure includes the alignment structure extending from the second connector interface to the third connector interface; and
at least one of:
 (b) the second connector interface has fewer contacts than the third connector interface, and the electrical connections electrically connect the plurality of the contacts of the third connector interface to the single contact of the second connector interface;
 (c) the electrical connections are configured to convert the first voltage applied to the third connector interface to the second voltage at the second connector interface, and the first voltage is different from the second voltage; or
 (d) the x-ray detector comprises control logic coupled to the first connector interface, and the control logic is configured to:
  present the first functional interface at the third connector interface;
  present the second functional interface at the second connector interface; and
  convert at least one of:
   the first functional interface to the second functional interface; and
   the second functional interface to the first functional interface.

7. The x-ray system of claim 1, wherein:
the housing of the x-ray detector comprises a recess; and
the adapter is configured to be integrated with the x-ray detector in the recess.

8. The x-ray system of claim 1, wherein:
the second connector interface has fewer contacts than the third connector interface;
the electrical connections electrically connect the plurality of the contacts of the third connector interface to the single contact of the second connector interface; and
at least one of:
 (a) the third connector interface includes at least one alignment structure extending from the second connector interface to the third connector interface;
 (c) the electrical connections are configured to convert the first voltage applied to the third connector interface to the second voltage at the second connector interface, and the first voltage is different from the second voltage; or
 (d) the x-ray detector comprises control logic coupled to the first connector interface, and the control logic is configured to:
  present the first functional interface at the third connector interface;
  present the second functional interface at the second connector interface; and
  convert at least one of:
   the first functional interface to the second functional interface; and
   the second functional interface to the first functional interface.

9. The x-ray system of claim 1, wherein:
the electrical connections are configured to convert the first voltage applied to the third connector interface to the second voltage at the second connector interface;
the first voltage is different from the second voltage; and
at least one of:
 (a) the third connector interface includes at least one alignment structure extending from the second connector interface to the third connector interface;
 (b) the second connector interface has fewer contacts than the third connector interface, and the electrical connections electrically connect the plurality of the contacts of the third connector interface to the single contact of the second connector interface; or
 (d) the x-ray detector comprises control logic coupled to the first connector interface, and the control logic is configured to:
  present the first functional interface at the third connector interface;
  present the second functional interface at the second connector interface; and
  convert at least one of:
   the first functional interface to the second functional interface; and
   the second functional interface to the first functional interface.

10. The x-ray system of claim 1, wherein:
the electrical connections are configured to at least one of:
 convert of signals received at the third connector interface in a first format to a second format; and
 convert signals received at the second connector interface in the second format to the first format.

11. The x-ray system of claim 1, wherein:
the adapter comprises control logic coupled to the second connector interface and the third connector interface; and
the control logic is configured to:
 present a first functional interface at the third connector interface;
 present a second functional interface at the second connector interface; and
 convert between the first functional interface and the second functional interface.

12. The x-ray system of claim 1, wherein:
the x-ray detector comprises control logic coupled to the first connector interface;
the control logic is configured to:
 present the first functional interface at the third connector interface;
 present the second functional interface at the second connector interface; and
 convert at least one of:
  the first functional interface to the second functional interface; and
  the second functional interface to the first functional interface; and at least one of:
 (a) the third connector interface includes at least one alignment structure extending from the second connector interface to the third connector interface;
 (b) the second connector interface has fewer contacts than the third connector interface, and the electrical connections electrically connect the plurality of the contacts of the third connector interface to the single contact of the second connector interface; or
 (c) the electrical connections are configured to convert the first voltage applied to the third connector interface to the second voltage at the second connector interface, and the first voltage is different from the second voltage.

13. The x-ray system of claim 1, wherein:
the adapter comprises a seal extending around the second connector interface and configured to form a seal with the x-ray detector when the adapter is attached to the x-ray detector.

14. The x-ray system of claim 1, wherein:
the adapter comprises a stiffener.

15. A method, comprising:
receiving a signal having a first format, at an adapter attached to an exterior of a housing of an x-ray detector, associated with an acquisition by the x-ray detector;
converting the signal having the first format into a signal having a second format in the adapter attached to the x-ray detector; and
performing the acquisition by the x-ray detector in response to the signal having the second format.

16. The method of claim 15, further comprising:
receiving a first voltage at the adapter;
converting the first voltage into a second voltage in the adapter; and
supplying the second voltage to the x-ray detector as a power supply.

17. The method of claim 15, wherein converting the signal having the first format into the signal having the second format in the adapter comprises:
presenting a first functional interface by the adapter; and
presenting a second functional interface by the adapter to the x-ray detector;
converting information received through the first functional interface into the second format for the second functional interface.

18. The method of claim 15, further comprising:
converting the signal having the second format into a signal having a third format in the x-ray detector.

19. An x-ray system, comprising:
means for receiving a signal having a first format, at an adapter attached to an exterior of a housing of an x-ray detector, associated with an acquisition by the x-ray detector;
means for converting the signal having the first format into a signal having a second format in the adapter attached to the x-ray detector; and
means for performing the acquisition by the x-ray detector in response to the signal having the second format.

20. The x-ray system of claim 19, further comprising:
means for presenting a first functional interface by the adapter;
means for presenting a second functional interface by the adapter to the x-ray detector; and
means for converting information received through the first functional interface into the second format for the second functional interface.

* * * * *